(12) United States Patent
Chung et al.

(10) Patent No.: US 10,987,295 B2
(45) Date of Patent: Apr. 27, 2021

(54) METHOD OF FACILITATING THE BINDINGS BETWEEN KERATINOCYTES

(71) Applicant: College of Medicine Pochon CHA University Industry-Academic Cooperation Foundation, Pocheon-si (KR)

(72) Inventors: Ji-Hyung Chung, Seoul (KR); Da-Yoon Chung, Pyeongtaek-si (KR)

(73) Assignee: College of Medicine Pochon CHA University Industry-Academic Cooperation Foundation, Pocheon-si (KR)

( * ) Notice: Subject to any disclaimer, the term of this patent is extended or adjusted under 35 U.S.C. 154(b) by 0 days.

(21) Appl. No.: 16/908,754

(22) Filed: Jun. 23, 2020

(65) Prior Publication Data

US 2020/0315941 A1  Oct. 8, 2020

Related U.S. Application Data

(62) Division of application No. 16/345,888, filed as application No. PCT/KR2017/012039 on Oct. 30, 2017, now Pat. No. 10,729,635.

(30) Foreign Application Priority Data

Oct. 31, 2016  (KR) .................. 10-2016-0143248

(51) Int. Cl.

| *A61K 8/64* | (2006.01) |
|---|---|
| *A61K 38/08* | (2019.01) |
| *A61K 38/10* | (2006.01) |
| *A61K 38/16* | (2006.01) |
| *A61Q 19/00* | (2006.01) |
| *A61Q 19/08* | (2006.01) |
| *C07K 7/06* | (2006.01) |
| *C07K 7/08* | (2006.01) |
| *C07K 14/00* | (2006.01) |
| *A61K 9/00* | (2006.01) |

(52) U.S. Cl.
CPC .............. *A61K 8/64* (2013.01); *A61K 9/0014* (2013.01); *A61Q 19/00* (2013.01); *A61Q 19/08* (2013.01); *C07K 7/06* (2013.01); *C07K 7/08* (2013.01); *C07K 14/00* (2013.01)

(58) Field of Classification Search
CPC ........ A61K 8/64; A61K 9/0014; A61K 38/08; A61K 38/10; A61K 38/16; A61Q 19/00; A61Q 19/08; C07K 14/00; C07K 7/06; C07K 7/08

USPC ......... 514/18.6, 18.8, 21.8, 21.7, 21.5, 21.4; 530/300, 329, 327, 326

See application file for complete search history.

(56) References Cited

U.S. PATENT DOCUMENTS

| 4,798,791 A | 1/1989 | Anderson et al. |
|---|---|---|
| 5,049,504 A | 9/1991 | Maugh et al. |
| 5,149,657 A | 9/1992 | Maugh et al. |
| 5,202,236 A | 4/1993 | Maugh et al. |
| 5,202,256 A | 4/1993 | Maugh et al. |
| 5,242,808 A | 9/1993 | Maugh et al. |
| 6,987,170 B1 | 1/2006 | Silverman et al. |
| 6,995,012 B1 | 2/2006 | Silverman et al. |
| 7,745,391 B2 * | 6/2010 | Mintz ................ A61P 31/00 514/19.3 |
| 8,957,189 B2 | 2/2015 | Wolf et al. |
| 10,478,392 B2 * | 11/2019 | Chung ................ A61K 8/64 |
| 2006/0029996 A1 | 2/2006 | Silverman et al. |
| 2006/0029997 A1 | 2/2006 | Silverman et al. |
| 2007/0083334 A1 | 4/2007 | Mintz et al. |
| 2012/0202397 A1 | 8/2012 | Wolf et al. |
| 2015/0152311 A1 | 6/2015 | Wolf et al. |
| 2018/0325794 A1 | 11/2018 | Chung |

FOREIGN PATENT DOCUMENTS

| JP | 2013-503625 A | 2/2013 |
|---|---|---|
| WO | 2006/020594 A2 | 2/2006 |
| WO | 2006/031327 A2 | 3/2006 |

OTHER PUBLICATIONS

G8JYP9 from UniProt, pp. 1-3. Integrated into UniProtKB/TrEMBL Jan. 25, 2012. (Year: 2012).*
A0A43UTU3 from UniProt, pp. 1-3. Integrated into UniProtKB/TrEMBL May 8, 2019. (Year: 2019).*
Holten-Andersen et al., "Mussel-designed Protective Coatings for Compliant Substrates", J Dent Res., 2008, vol. 87, No. 8, pp. 701-709.

* cited by examiner

*Primary Examiner* — Julie Ha
(74) *Attorney, Agent, or Firm* — Vorys, Sater, Seymour & Pease LLP; Mih Suhn Koh

(57) ABSTRACT

Provided is a novel peptide and a cosmetic composition for inhibiting a skin-aging or a skin-wrinkle formation including the same. The peptide has activities for facilitating the bindings between keratinocytes; and increasing the expressions of junction proteins significantly.

2 Claims, 1 Drawing Sheet
Specification includes a Sequence Listing.

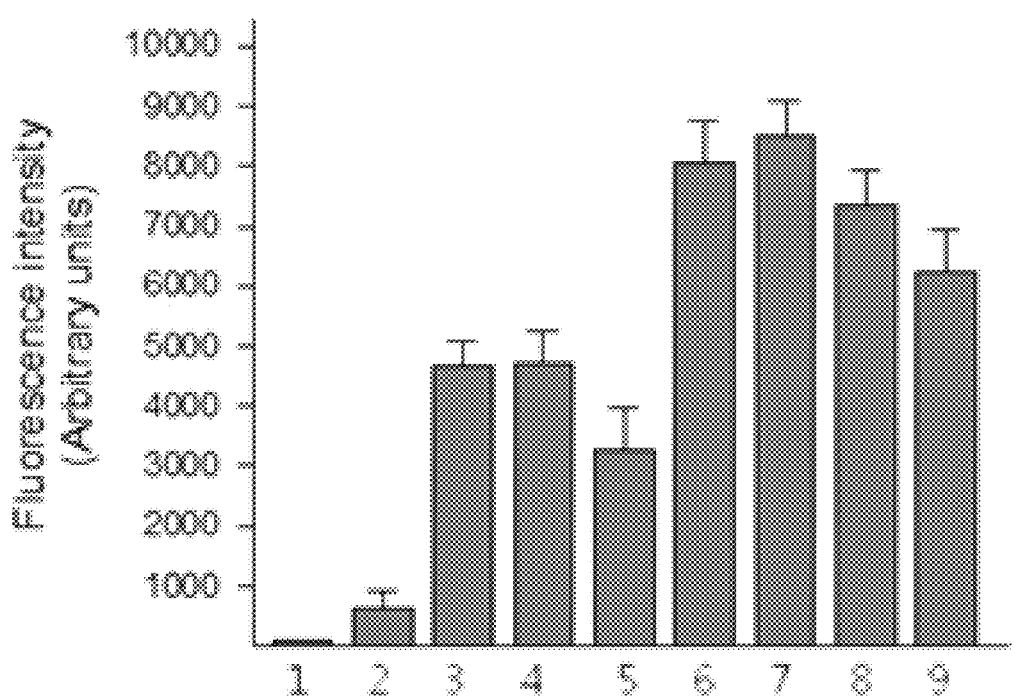

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Gly Arg Ala Leu Ala Arg Gly
1               5

```
<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Gly Arg Ala Leu Ala Arg Gly Gly Arg Ala Leu Ala Arg Gly
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Gly Arg Gly Asp Ser Pro Gly Arg Ala Leu Ala Arg Gly Gly Arg Ala
1               5                   10                  15

Leu Ala Arg Gly
            20

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ala Lys Pro Thr Tyr Lys
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Ala Lys Pro Thr Tyr Lys Ala Lys Pro Thr Tyr Lys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ala Tyr Asp Pro Gly Tyr Lys
1               5

<210> SEQ ID NO 7
<211> LENGTH: 21
<212> TYPE: PRT
<213> ORGANISM: Artificial Sequence
<220> FEATURE:
<223> OTHER INFORMATION: Synthetic peptide

<400> SEQUENCE: 7
```

-continued

```
Ala Tyr Asp Pro Gly Tyr Lys Ala Tyr Asp Pro Gly Tyr Lys Ala Tyr
1               5                   10                  15

Asp Pro Gly Tyr Lys
            20
```

METHOD OF FACILITATING THE BINDINGS BETWEEN KERATINOCYTES

SEQUENCE LISTING

The Sequence Listing submitted in text format (.txt) filed on Jun. 23, 2020, named "SequenceListing.txt", created on Apr. 22, 2019 (1.93 KB), is incorporated herein by reference.

TECHNICAL FIELD

The present invention relates to a peptide and a cosmetic composition for inhibiting a skin-aging or a skin-wrinkle formation comprising the same. The peptide has activities for facilitating the bindings between keratinocytes; and increasing the expressions of junction proteins.

BACKGROUND ART

Human skin consists of epidermis and dermis, besides the outermost layer thereof (keratin); and hypodermis containing adipose tissues resides thereunder. The epidermis consists mainly of keratinocytes; and the dermis consists mainly of dermal fibroblasts.

Functional cosmetic materials targeting for ameliorating wrinkle and inhibiting skin aging are mainly natural products, chemical compounds and peptides for facilitating the expression of collagen proteins in the dermal fibroblasts (major cells of the dermis) or inhibiting the proteases against collagen proteins; in addition to proteins such as growth factors, cytokines and the like, for facilitating the growth of dermal cells. However, it is well known in the art that it is very difficult for most active materials having such effects to pass through the epidermis of the skin and reach the dermis.

The epidermis acts as a barrier for preventing the permeation of external harmful substances, ultraviolet, chemical substances, and so on and maintaining the moisturization in the skin. The major cell functioning as such is keratinocytes and it is known in the art that keratinocytes regulate immune responses in the sub-dermal tissues by secreting inflammatory regulators (cytokines, chemokines, etc.), along with maintaining the skin barrier. It is known in the art that such a skin barrier function of the epidermis is originated from the bindings between keratinocytes, i.e., the expression and activation of cell-to-cell junction proteins. The junction proteins function as an important barrier not only for providing a primary physical defense from external infections, but also for protecting dermal cells and inhibiting immune imbalance from chemical stimulations inside or outside the cells. The junction proteins are usually divided into four groups: tight junction proteins, adherence junction proteins, gap junction proteins, and desmosomes. Among them, tight junction proteins (e.g., claudins, occludins, ZO-1, 2, etc.) are known as a major factor contributing to the cell barrier protection, by preventing the migration of molecules, especially water-soluble materials, through the space between cells; and inhibiting cell permeability. Therefore, it is expected that a material capable of facilitating the bindings between keratinocytes and/or increasing the expressions of junction proteins may be useful for inhibiting a skin-aging or a skin-wrinkle formation, through protection and activation of the skin barrier.

DISCLOSURE

Technical Problem

The present inventors have synthesized various peptide fragments and evaluated the activities thereof. As the results thereof, it has been found that the peptide fragments having specific sequences show activities for facilitating the bindings between keratinocytes effectively; and increasing the expressions of junction proteins significantly.

Therefore, it is an object of the present invention to provide said peptide fragments.

It is another object of the present invention to provide a cosmetic composition for inhibiting a skin-aging or a skin-wrinkle formation, comprising said peptide fragments.

Technical Solution

In accordance with an aspect of the present invention, there is provided a peptide having any one of amino acid sequences of SEQ ID NOs: 1 to 7.

In accordance with another aspect of the present invention, there is provided a cosmetic composition for inhibiting a skin-aging or a skin-wrinkle formation, comprising a peptide having any one of amino acid sequences of SEQ ID NOs: 1 to 7.

Advantageous Effects

It has been found by the present invention that the specific peptide fragments, i.e., to the peptides as set forth in SEQ ID NOs: 1 to 7, show activities for facilitating the bindings between keratinocytes effectively; and increasing the expressions of junction proteins significantly. Therefore, the peptides can be usefully applied to a cosmetic composition for inhibiting a skin-aging or a skin-wrinkle formation.

BRIEF DESCRIPTION OF THE DRAWINGS

The FIGURE shows the results obtained by evaluating the binding efficacies between keratinocytes through the cell-cell interaction assays using human epidermal keratinocytes. Lane 1 shows the result of the group in which the cultured cells were not treated with the binding cells (i.e., the stained cells) (Control group 1); Lane 2 shows the result of the group in which the cultured cells were treated with the binding cells (i.e., the stained cells) (Control group 2); and Lanes 3 to 9 shows the results of the groups in which the cultured cells were pre-treated with each peptide of SEQ ID NOs: 1 to 7 and then treated with the binding cells (i.e., the stained cells).

BEST MODE

As used herein, the term, "skin aging" refers to the skin aging(s) caused by intrinsic and external factors, including for example the skin photoaging(s) accompanied by skin-wrinkle formation, preferably the skin photoaging(s) due to ultraviolet stimulation accompanied by skin-wrinkle formation.

And also, the "skin wrinkle" refers to the wrinkles formed on the skin (wrinkle formation on skin).

The present invention provides a peptide having any one of amino acid sequences of SEQ ID NOs: 1 to 7.

And also, the present invention provides a cosmetic composition for inhibiting a skin-aging or a skin-wrinkle formation, comprising a peptide having any one of amino acid sequences of SEQ ID NOs: 1 to 7.

The present inventors have synthesized various peptide fragments and evaluated the activities thereof. Surprisingly, it has been found that the peptide fragments having to specific sequences, i.e., the peptide as set forth in SEQ ID NOs: 1 to 7, not only facilitate physical bindings between the keratinocytes, major cells in the epidermis which contribute to protection and activation of the skin barrier, but also increase the expressions of junction proteins significantly. Therefore, the peptides according to the present invention can be usefully applied to a cosmetic composition for improving a skin-aging is and/or inhibiting a skin-wrinkle formation. The peptides as set forth in SEQ ID NOs: 1 to 7 may be synthesized according to conventional methods for synthesizing a peptide.

The cosmetic composition of the present invention may be in the form of a functional cosmetic composition comprising said peptides as an active ingredient. The cosmetic composition may be prepared in various forms according to conventional methods thereof. For example, the cosmetic composition may be prepared in forms of cosmetic products, cosmetic solutions, creams, lotions, etc. comprising said peptides, which may be diluted with a cleansing water, an astringent solution, or a moisture solution, for the use thereof. And also, the cosmetic composition may include conventional excipients, such as a stabilizer, a solubilizing agent, vitamins, a pigment, a flavoring agent, which are conventionally used in the field of cosmetic composition. In the cosmetic composition, the peptides may be present in an amount enough to provide improvement of a skin-aging and/or inhibition of a skin-wrinkle formation, for example in an amount ranging from 0.001 to 2 weight %, preferably about 0.1 to 2 weight %, based on the total weight of the composition.

Hereinafter, the present invention will be described more specifically by the following examples. However, the following examples are provided only for illustrations and thus the present invention is not limited to or by them.

Example 1: Synthesis of Peptides

The peptides of SEQ ID NOs: 1 to 7 in the following table 1 were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and to identified using a mass spectrometer (HP 1100 Series LC/MSD, Hewlett-Packard, Roseville, U.S.A.).

TABLE 1

| Peptide name* | SEQ ID NO | Amino acid sequence (sequence length) |
|---|---|---|
| AdhPep-5-1 | SEQ ID NO: 1 | GRALARG (7-mer) |
| AdhPep-5-2 | SEQ ID NO: 2 | GRALARGGRALARG (14-mer) |
| AdhPep-5-3 | SEQ ID NO: 3 | GRGDSPGRALARGGRALARG (20-mer) |
| AdhPep-10 | SEQ ID NO: 4 | AKPTYK (6-mer) |
| AdhPep-10-1 | SEQ ID NO: 5 | AKPTYKAKPTYK (12-mer) |
| AdhPep-11 | SEQ ID NO: 6 | AYDPGYK (7-mer) |
| AdhPep-11-2 | SEQ ID NO: 7 | AYDPGYKAYDPGYKAYDPGYK (21-mer) |

*Peptide name: arbitral name for experiments

Example 2: Evaluation of the Binding Efficacies Between Keratinocyte

The cell-cell interaction assay was carried out in order to evaluate the binding efficacies between keratinocytes. Human epidermal keratinocytes (Thermo Fisher Scientific) were inoculated in the concentration of $5 \times 10^4$ cells in each well of a 24-well plate; and the EpiLife medium (Thermo Fisher Scientific) containing Human Keratinocyte Growth Supplement (Thermo Fisher Scientific) was added thereto. The cells were cultured in a $CO_2$ incubator for 24 hours. Each well was treated with the peptides of SEQ ID NOs: 1 and 7 in the concentration of 100 nM. After incubating for 40 minutes, the medium of each well was changed. Human epidermal keratinocytes were stained with Vybrant DiO Cell-labeling dye (Life Technologies). The stained cells ($1.5 \times 10^5$ cells) were treated to the cells treated with the respective peptides, followed by incubating for 10 minutes. For comparison, Control group 1 is the group in which the cultured cells were not treated with the binding cells (i.e., the stained cells); and Control group 2 (the peptide non-treated group) is the group in which the cultured cells were treated only with the binding cells. After washing the cells of each group with phosphate-buffered saline (PBS) three times, the cells were detached with a cell stripper solution and then transferred to a black well plate. Each fluorescence intensity was measured at the to wavelengths of 480/501 nm and the results thereof are shown in the FIGURE. As can be seen from the results shown in the FIGURE, the bindings between keratinocytes in the test groups treated with the peptides of SEQ ID NOs: 1 to 7 were remarkably increased, in comparison with that of the peptide non-treated group (Control group 2).

The invention claimed is:

1. A peptide consisting of the amino acid sequence of SEQ ID No: 7.

2. A method of facilitating the bindings between keratinocytes in a subject in need thereof, comprising applying a cosmetic composition comprising the peptide consisting of the amino acid sequence of SEQ ID No: 6 or 7 as an active ingredient to the skin of the subject.

* * * * *